(12) United States Patent
Hickey

(10) Patent No.: US 6,432,059 B2
(45) Date of Patent: Aug. 13, 2002

(54) METHOD AND APPARATUS FOR MORE PRECISELY DETERMINED MEAN LEFT ATRIAL PRESSURE

(75) Inventor: Donald D. Hickey, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/855,935

(22) Filed: May 15, 2001

Related U.S. Application Data

(60) Continuation-in-part of application No. 09/625,329, filed on Jul. 25, 2000, now Pat. No. 6,238,349, which is a division of application No. 09/097,252, filed on Jun. 12, 1998, now Pat. No. 6,120,442.
(60) Provisional application No. 60/049,459, filed on Jun. 12, 1997.

(51) Int. Cl.$^7$ .................................................. A61B 5/00
(52) U.S. Cl. ........................ 600/486; 600/561; 600/593
(58) Field of Search ................................ 600/486, 488, 600/561, 593

(56) References Cited

U.S. PATENT DOCUMENTS

| 5,048,532 A | * | 9/1991 | Hickey | 600/486 |
| 5,263,485 A | * | 11/1993 | Hickey | 600/486 |

* cited by examiner

Primary Examiner—Robert L. Nasser
(74) Attorney, Agent, or Firm—James C. Simmons

(57) ABSTRACT

A method and apparatus for more precisely determining mean left atrial pressure. A catheter including a balloon is inserted into an esophagus with the balloon positioned adjacent the left atrium and inflated to provide a signal of balloon pressure oscillations effected by the left atrium. By use of the fast Fourier transform, the amplitude of each of simple harmonic wave forms (or a corresponding portion thereof) making up the balloon pressure oscillation signal is corrected for characteristics of the catheter and the corrected wave forms combined into a corrected signal of balloon pressure oscillations. The balloon pressure is measured when the amplitude of the corrected balloon pressure oscillation signal is at a peak, wherein the measured balloon pressure is determined to be mean left atrial pressure.

3 Claims, 2 Drawing Sheets

METHOD AND APPARATUS FOR MORE PRECISELY DETERMINED MEAN LEFT ATRIAL PRESSURE

This is-a continuation-in-part of pending application Ser. No. 09/625,329, filed Jul. 25, 2000 now U.S. Pat. No. 6,238,349, which is a division of application Ser. No. 09/097,252, filed Jun. 12, 1998 (now U.S. Pat. No. 6,120,442), which claims priority of U.S. provisional patent application Ser. No. 60/049,459, filed Jun. 12, 1997. These prior applications are hereby incorporated herein by reference.

The pre-sent invention relates generally to an apparatus and method for noninvasive monitoring of one or more cardiac performance parameters, and more particularly to a method and an apparatus determining mean left atrial pressure.

The diagnosis and care of patients with cardiovascular disease critically depends on information about the pumping ability of the heart. For example, the priming pressure of the left ventricle of the heart, typically obtained by measurement of left atrial pressure, indicates, when abnormal, a mismatch between volume capacity of the vascular system and the circulatory blood volume.

Since the early 1970's, the flow-directed pulmonary artery balloon catheter (a.k.a. the Swan-Ganz catheter) has been the standard for bedside hemodynamic monitoring. It yields cardiac output by thermodilution as well as an estimate of mean left atrial pressure. However, under certain conditions, the pressure readings may not faithfully reflect left atrial pressure (R. RAPER et al, "Misled by the Wedge", Chest, March 1986, pp. 427–434). This invasive technique is personnel intensive and costly since the catheter must be inserted and used in a critical care area or operating room, and it has been associated with infection, arrhythmias, and death (E. ROBIN et al, "The Cult of the Swan-Ganz Catheter", Annals of Internal Medicine, September 1985, vol. 103, pp. 445–449). Its use is further limited since it only provides non-automated intermittent measurements, and the catheter should, for safety reasons, only be left in the patient for a few days.

My U.S. Pat. Nos. 5,048,532; 5,181,517; 5,263,4.85; 5,398,692; 5,551,439; 5,570,671; 5,697,375; and 5,921,935, the disclosures of all of which patents are incorporated herein by reference, disclose noninvasive methods and apparatus which includes a catheter containing an inflatable balloon insertable into the esophagus for placement adjacent the left atrium, and associated equipment for making determinations of-mean left atrial pressure. When the inflated balloon is adjacent the left atrium and receiving pressure waves therefrom, the balloon pressure oscillates. As the balloon pressure is gradually increased, the balloon oscillations reach a peak or point of maximum oscillatory amplitude. As discussed in my prior patents, this peak is believed to occur when the balloon pressure is equal to the mean left atrial pressure. Thus, a determination of mean left atrial pressure may be made by noting the balloon pressure at the oscillatory peak.

As discussed in the parent patent to this application, the mean left atrial pressure as determined above may be used in conjunction with the effects of aortic pressure on an inflated balloon to noninvasively and more comprehensively provide cardiac performance information.

While the above technique for determining mean left atrial pressure has been shown experimentally to be accurate, there have nevertheless been instances where the mean left atrial pressure as determined by the above technique has tended to be over estimated, i.e., showing a greater mean left atrial pressure than the actual mean left atrial pressure.

It is accordingly an object of this invention to noninvasively and more precisely determine mean left atrial pressure.

In order to noninvasively and more precisely determine mean left atrial pressure, in accordance with the present invention, the wave form of the balloon pressure oscillations is subjected to fast Fourier transform analysis to apply a catheter transfer function to each of the component waves thereof to correct the amplitudes thereof, and a corrected wave form reconstructed from the corrected component waves.

The above and other objects, features, and advantages of this invention will become apparent to those skilled in the art after a consideration of the following detailed description taken in conjunction with the accompanying drawings wherein the same reference numerals denote the same or similar parts or items throughout the several views and in which a preferred embodiment of this invention is illustrated.

DETAILED DESCRIPTION OF THE PREFERRED EMBODIMENT

Figure 1:
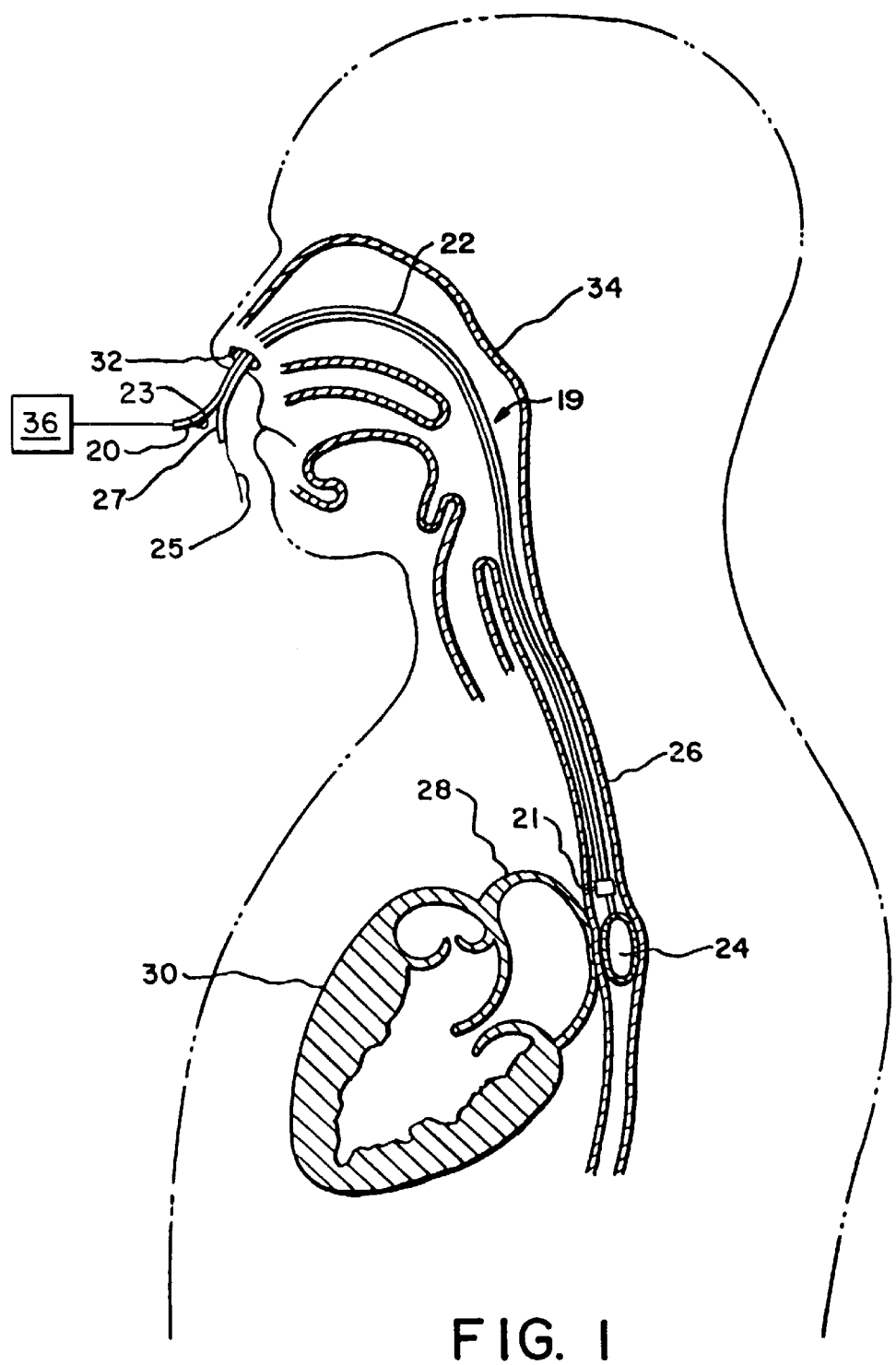
FIG. 1 is a partial left lateral sectional view of the human body taken along the mid-sagittal plane and showing a balloon-containing catheter in accordance with the present invention within the esophagus and adjacent the left atrium of the heart.
Figure 2:
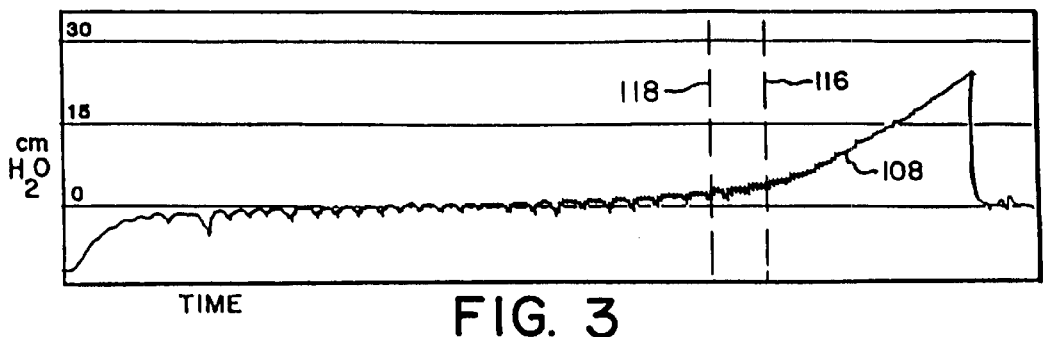
FIG. 2 is a pressure trace of an unfiltered signal of balloon pressure with respiratory and cardiac-effected oscillations when the balloon is adjacent the left atrium, as the balloon is gradually inflated.
Figure 3:
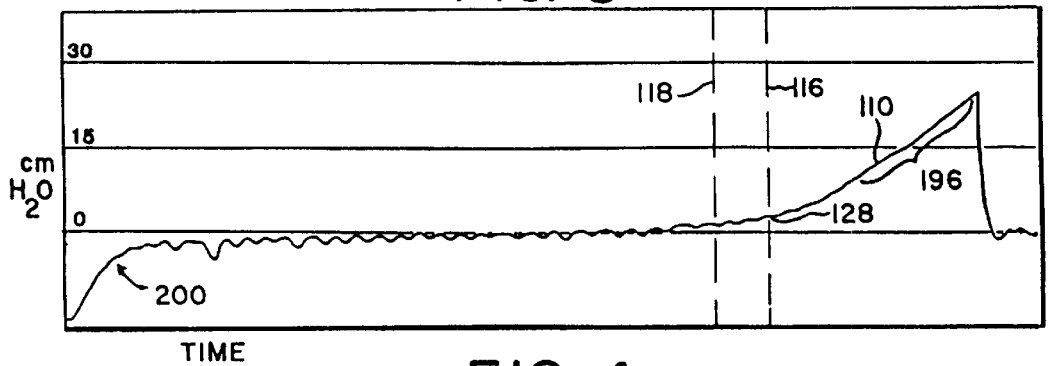
FIG. 3 is a pressure trace of mean balloon pressure for the pressure trace of FIG. 2.
Figure 4:
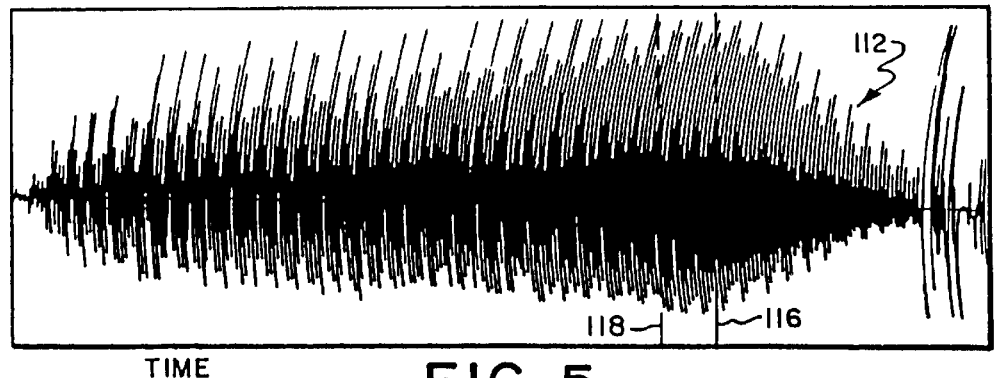
FIG. 4 is a pressure trace of amplified cardiac signal on a steady baseline which signal is derived from the balloon pressure trace of FIG. 2 and covers the same time period as that of FIGS. 2 and 3.

Referring to FIG. 1, there is illustrated generally at 19 catheter apparatus including a hollow catheter 20 comprising a length of flexible tubing 22 having a bore or lumen 23 and on one end of which is attached a balloon 24 for flow communication with the lumen 23 for pressurization of the balloon and for sensing the pressure thereof. If desired, an electrode 21 may be positioned just above the balloon 24 for obtaining an esophageal electrocardiogram and an electrical lead 25, within a second catheter 27, provided thereto.

There is also illustrated in FIG. 1 the placement of the balloon 24 within the esophagus 26 of a human body for the purpose of sensing the mean pressure of the left atrium 28 of the heart 30. The catheter 20 is inserted balloon first through nasal passage 32, pharynx 34, then into the esophagus 26. If desired, the balloon may be alternatively inserted through the mouth. As shown in FIG. 1, the outer wall of the left atrium 28 is adjacent and essentially in direct contact with the outer wall of the esophagus 26, and advantage is taken of this relationship to determine mean left atrial pressure by means of the balloon 24 thusly inserted noninvasively into the esophagus 26 and positioned therealong adjacent the left atrium so as to be sufficiently affected thereby to sense left atrial pressure, as will be discussed in greater detail hereinafter. The catheter apparatus is described in greater detail in my aforesaid prior patents and, in the interest of brevity, will not be repeated here.

It should of course be understood that balloon 24 and determinations of mean left atrial pressure obtained therewith may be used in conjunction with a second balloon which senses aortic pressure for providing various cardiac performance parameters noninvasively and comprehensively, as described in my aforesaid parent '442 patent.

Figure 5:
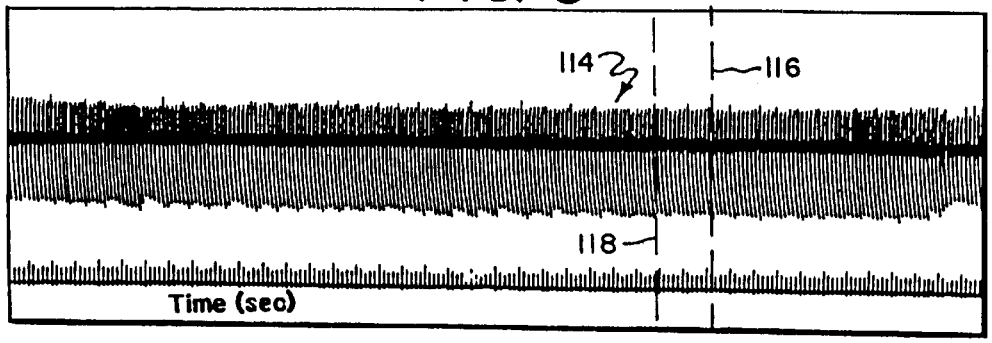
FIG. 5 is a graph of an electrocardiogram taken simultaneously with the pressure traces of FIGS. 2, 3, and 4.

FIGS. 2 to 5 are illustrations of four electronic displays or tracings used to record and display the absolute balloon pressure wave form 108 (FIG. 2), the mean balloon pressure wave form 110 (FIG. 3), the differential signal 112 (FIG. 4) with added gain from a signal processor (not shown), and a simultaneous electrocardiogram 114 (FIG. 5). Vertical line 116 in each of FIGS. 2 to 5 represents the same point in time. As discussed in my aforesaid prior patents, the absolute balloon pressure wave form is preferably filtered or otherwise processed to remove low frequency artifacts such as from respiration or peristalsis to derive wave form 112.

While not wishing to be bound by theory here or elsewhere in this specification, the following is believed to occur as the sensing balloon 24 is pressurized. The gradual filling of the sensing balloon 24 causes the pressure therein to increase at a generally slow steady rate which, in accordance with the oscillometric principle, is affected by the atrial pressure causing oscillations therein as well as respiratory waves (which as discussed above should be filtered out). As the mean balloon pressure approaches the mean left atrial pressure, the left atrial pressure oscillations superimposed on the balloon pressure signal increase in intensity or amplitude until the balloon pressure signal resonates maximally, i.e., reaches a peak amplitude, when the mean balloon pressure approximates the mean left atrial pressure. Thereafter, as the mean balloon pressure continues to increase, the amplitude of oscillations due to the left atrial pressure decreases. More specifically, the balloon pressure oscillates maximally when its expansion has increased the pressure in the tissue surrounding the left atrium to the point where the mean tissue pressure equals the mean left atrial pressure.

The wave form 112 is an oscillating signal of varying amplitude on a steady baseline. These oscillations, derived from the absolute balloon pressure signal, are in response to the driving pressure of the left atrium. By noting the peak resonant amplitude of the wave form 112 (FIG. 4) and comparing it to the simultaneous mean balloon pressure 110 (FIG. 3), an approximation of the mean left atrial pressure can be determined. Thus, in accordance with the oscillometric principle, the mean balloon pressure approximates the mean left atrial pressure when the oscillations of wave form 112 are at a peak, i.e., the peak or highest amplitude oscillations in the wave form 112 occur at the time 116 the balloon pressure is equal to mean left atrial pressure. An approximation of mean left atrial pressure is thus determined from the example of FIGS. 2 to 5 to be a pressure, illustrated at 128, of about 3 cm water.

While the above technique for determining mean left atrial pressure has been shown experimentally to be accurate, there have nevertheless been instances where the mean left atrial pressure as determined by the above technique has tended to be over-estimated, i.e., showing a greater mean left atrial pressure than the actual mean left atrial pressure. It is believed that this may be due to distortions in amplitudes of the signal 112 as a result of the distance (for example, 180 cm) over which the signal 112 must travel in the tubing 22 to be processed.

In order to noninvasively and more precisely provide a non-distorted signal of balloon pressure oscillations to determine mean left atrial pressure, in accordance with the present invention, the signal 112 of balloon pressure oscillations is subjected to fast Fourier transform analysis and corrected to eliminate such distortions. In accordance with Fourier's theorem, any repetitive wave form such as signal 112 is the sum of simple harmonic wave forms. By use of fast Fourier transform analysis, which is a technique commonly known to those of ordinary skill in the art to which this invention pertains, the component wave forms, each having a different frequency, of the signal 112 are identified along with their amplitudes (the signal is separated into its component wave forms), for example, a fundamental sine wave having a frequency of 1 Hertz and a sin wave having a frequency of 6 Hertz and 1/20 of the amplitude of the fundamental and perhaps other wave forms.

Each frequency may undergo a different amount of distortion in the specific tubing 22 so that, for example, the 1 Hertz frequency wave form may have its amplitude reduced by only a small amount while the 6 Hertz frequency wave form may have its amplitude reduced by a much larger amount. In order to determine for the tubing 22 how much distortion each frequency component undergoes, a series of wave forms of different frequencies are transmitted through the tubing 22 and the input or source amplitude of each wave form is compared to the output amplitude measured at the end of the tubing to derive a transfer function for the amplitude for each frequency. If desired, a transfer function may also be derived for phase shift for each frequency.

In accordance with the present invention, to the amplitude of each component wave form of signal 112 is applied the transfer function for its frequency to provide a corrected amplitude for each frequency component. For example, for a 1 Hertz wave form, the transfer function may be 120%, i.e., the amplitude is increased by 20%, while for a 6 Hertz wave form, the transfer function may be 180%, i.e., the amplitude is increased by 80%. If desired, a similar process may be followed for phase shift. An equation may be developed for the transfer function for amplitude and, if desired, phase shift, at any given frequency, and this regression equation applied to each frequency component.

Finally, a corrected signal more precisely representative of the true left atrial pressure wave form is formed by using inverse fast Fourier transform analysis, i.e., by adding together the amplitude-corrected wave forms.

In the specific application using tubing similar to tubing 22, the application of fast Fourier transform analysis has resulted in increased amplitudes for higher frequency components as compared to lower frequency components, which means that the peak would be expected to occur earlier and therefore at a lower pressure in some instances. The application of the above fast Fourier transform process to balloon signals similar to signal 112 should result in the peak amplitude occurring at an earlier point (lower pressure) than the location of the peak when the signal is not subjected to fast Fourier transform analysis, which is consistent with the observation that the mean left atrial pressure has sometimes tended to be estimated to be higher than the true mean left atrial pressure. For example, the corrected peak may perhaps be located as illustrated at 118 in FIGS. 2 to 5.

Referring to FIG. 1, the balloon pressure oscillation signal 112 is suitably processed, in accordance with principles commonly known to those of ordinary skill in the art to which this invention pertains, in a suitably programmed general purpose computer, illustrated at 36, to derive the corrected balloon pressure oscillation signal which provides the corrected peak 118.

My aforesaid parent '442 patent discloses using the peak of a corresponding portion of the left atrial pressure signal, i.e., the "a" wave portion, for determining mean left atrial pressure, i.e., measuring the balloon pressure when the amplitude of the corresponding portions is at a peak. The above fast Fourier transform process may be applied to such a signal portion.

By "signal of balloon pressure oscillations", as used herein and in the claims, is meant to include, heart sounds passing through the inflated balloon and recorded by a microphone, as discussed in my aforesaid U.S. Pat. Nos. 5,697,375 and 5,921,935.

Although the invention has been described in detail herein, it should be understood that the invention can be embodied otherwise without departing from the principles thereof, and such other embodiments are meant to come within the scope of the present invention as defined by the appended claims.

What is claimed is:

1. Apparatus for determining mean left atrial pressure comprising a catheter including an inflatable balloon insertable into an esophagus; means for sensing a signal of balloon pressure oscillations effected by the left atrium when the balloon is inflated and in the esophagus adjacent the left atrium; means for correcting the amplitude of at least a corresponding portion of each of simple harmonic wave forms making up the balloon pressure oscillation signal for characteristics of the catheter and for combining the corrected wave forms into a corrected signal of balloon pressure oscillations; and means for measuring the balloon pressure when the amplitude of the corrected balloon pressure oscillation signal is at a peak, wherein the measured balloon pressure is determined to be mean left atrial pressure.

2. A method of determining mean left atrial pressure comprising the steps of:

a. inserting a catheter including a balloon into an esophagus;

b. positioning the balloon adjacent the left atrium;

c. inflating the balloon;

d. sensing a signal of balloon pressure oscillations effected by the left atrium;

e. correcting the amplitude of at least a corresponding portion of each of simple harmonic wave forms making up the balloon pressure oscillation signal for characteristics of the catheter and combining the corrected wave forms into a corrected signal of balloon pressure oscillations; and f. measuring the balloon pressure when the amplitude of the corrected balloon pressure oscillation signal is at a peak, wherein the measured balloon pressure is determined to be mean left atrial pressure.

3. A method of-determining mean left atrial pressure comprising the steps of:

a. inserting a catheter including a balloon into an esophagus;

b. positioning the balloon adjacent the left atrium;

c. inflating the balloon;

d. sensing a signal of balloon pressure oscillations effected by the left atrium;

e. correcting the amplitude of each of simple harmonic wave forms making up the balloon pressure oscillation signal for characteristics of the catheter and combining the corrected wave forms into a corrected signal of balloon pressure oscillations; and f. measuring the balloon pressure when the amplitude of the corrected balloon pressure oscillation signal is at a peak, wherein the measured balloon pressure is determined to be mean left atrial pressure.

\* \* \* \* \*